United States Patent
Frielinghaus et al.

(10) Patent No.: US 12,197,637 B2
(45) Date of Patent: *Jan. 14, 2025

(54) MEDICAL AUGMENTED REALITY NAVIGATION

(71) Applicant: Brainlab AG, Munich (DE)

(72) Inventors: Nils Frielinghaus, Heimstetten (DE); Christoffer Hamilton, Aschheim (DE)

(73) Assignee: BRAINLAB AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/947,828

(22) Filed: Sep. 19, 2022

(65) Prior Publication Data

US 2023/0016227 A1   Jan. 19, 2023

Related U.S. Application Data

(63) Continuation of application No. 16/478,065, filed as application No. PCT/EP2017/055689 on Mar. 10, 2017, now Pat. No. 11,460,915.

(51) Int. Cl.
*G06F 3/01* (2006.01)
*A61B 90/00* (2016.01)
(Continued)

(52) U.S. Cl.
CPC ............ *G06F 3/012* (2013.01); *A61B 90/361* (2016.02); *G02B 27/017* (2013.01);
(Continued)

(58) Field of Classification Search
CPC .............................. G06T 19/006; G06F 3/012
See application file for complete search history.

(56) References Cited

U.S. PATENT DOCUMENTS

2005/0203367 A1   9/2005   Ahmed et al.
2013/0245461 A1*  9/2013   Maier-Hein ......... A61B 90/361
                                                              600/476

(Continued)

FOREIGN PATENT DOCUMENTS

| WO | WO2005088539 | 9/2005 |
| WO | WO2012062482 | 5/2012 |
| WO | WO2018162078 | 9/2018 |

OTHER PUBLICATIONS

European Patent Office, International Search Report and Written Opinion for PCT Application No. PCT/EP2017/055689 dated Jun. 7, 2017.

*Primary Examiner* — Yi Yang (74) *Attorney, Agent, or Firm* — Gray Ice Higdon (57) ABSTRACT

The disclosed method encompasses registering an augmented reality device such as augmented reality glasses with a tracking coordinate system associated with a position tracking system. This may be effected by different approaches, for example by using a distance measurement unit (depth sensor) of the augmented reality device to determine a position of the augmented reality device relative to an object in a medical environment such as in surgery or radiotherapy/radiosurgery. The object may additionally be tracked by the position tracking system so that on the basis of the distance measurement, a relative position between the augmented reality device and the tracking coordinate system can be determined in order to register the augmented reality device with the position tracking system. This registration allows displaying augmentation information in a desired context and/or at a desired location in the image of the medical environment captured by the augmented reality device.

10 Claims, 6 Drawing Sheets

(51) Int. Cl.
*G02B 27/01* (2006.01)
*G06T 19/00* (2011.01)

(52) U.S. Cl.
CPC ...... *G06T 19/006* (2013.01); *A61B 2090/365* (2016.02); *G02B 2027/0138* (2013.01); *G02B 2027/014* (2013.01); *G02B 2027/0178* (2013.01); *G02B 2027/0187* (2013.01); *G06T 2207/30004* (2013.01)

(56) References Cited

U.S. PATENT DOCUMENTS

| | | | |
|---|---|---|---|
| 2014/0049629 A1* | 2/2014 | Siewerdsen | A61B 34/20 348/77 |
| 2015/0062000 A1 | 3/2015 | Saito | |
| 2016/0104486 A1* | 4/2016 | Penilla | G10L 15/02 704/232 |
| 2016/0133230 A1* | 5/2016 | Daniels | G06F 3/147 345/633 |
| 2016/0191887 A1 | 6/2016 | Casas | |
| 2016/0249989 A1 | 9/2016 | Devam et al. | |

* cited by examiner

MEDICAL AUGMENTED REALITY NAVIGATION

The present invention relates to a computer-implemented medical method for outputting, by an augmented reality device having a distance measurement unit, augmentation information relating to positional tracking by a medical position tracking system. The invention also relates to a computer configured to execute a program corresponding to the method and a medical system for determining augmentation information relating to positional tracking by a medical position tracking system, the medical system comprising a computer of the aforementioned kind.

TECHNICAL BACKGROUND

While augmented reality systems increasingly substitute regular displays of surgical navigation systems and radiation therapy positioning systems, the use of additional tracking technologies like optical, electromagnetic or articulated arm tracking will remain prevalent. This is due to the fact that augmented reality systems typically will not provide the same accuracy and field of view as required for surgical navigation and patient positioning.

A frequent complaint when using current tracking technologies is that the user cannot comprehend easily why the tracking does not work at a certain point of time due to line of sight to one tracking array being obstructed or the field of view being off target. The aim of this invention is to provide feedback on these conditions or avoid them through augmentation of the user's view.

A subset of augmented reality devices incorporate depth sensors (distance sensors) to map the surroundings and improve the reality-feeling of augmented content. In this invention these depth sensors are used in combination with tracking devices. Information derived from the combination of depth sensors and tracking sensors is displayed on the augmented reality device.

The present invention is designed to provide a method of combining a real image of a medical environment with additional manner by using augmented reality information.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses registering an augmented reality device such as augmented reality glasses with a tracking coordinate system associated with a position tracking system. This may be effected by different approaches, for example by using a distance measurement unit (depth sensor) of the augmented reality device to determine a position of the augmented reality device relative to an object in a medical environment such as in surgery or radiotherapy/radiosurgery. The object may additionally be tracked by the position tracking system so that on the basis of the distance measurement, a relative position between the augmented reality device and the tracking coordinate system can be determined in order to register the augmented reality device with the position tracking system. This registration allows displaying augmentation information in a desired context and/or at a desired location in the image of the medical environment captured by the augmented reality device.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented medical method for outputting, by an output unit of an augmented reality device having a distance measurement unit, augmentation information relating to positional tracking by a medical position tracking system.

Augmented reality (AR) is a live direct or indirect view of a physical, real-world environment whose elements are augmented (or supplemented) by computer-generated sensory input such as sound, video, graphics or GPS data.

The method according to the first aspect is for example a data processing method. The method according to the first aspect comprises executing, on at least one processor of at least one computer (for example at least one computer being part of a position tracking system), the following exemplary steps which are executed by the at least one processor.

In a (for example first) exemplary step, a viewing direction of the augmented reality device is positionally registered with a tracking coordinate system associated with the position tracking system to generate an augmented reality device registration. Registering the viewing direction with the tracking coordinate system means for example determining a spatial relationship (i.e. at least one of position or orientation, defined in for example 2, 3 or 6 dimensions or degrees of freedom) of the viewing direction (embodied by a vector which is defined in two or three directions, for example relative to the augmented reality device) in the tracking coordinate system.

For example, the display of the augmented reality device comprises a head-mounted display (a head-mounted display unit). Specifically, the display of the augmented reality device may be included in glasses (eyeglasses) wearable by a user. A head-mounted display (HMD) is a display device paired to the forehead such as a harness or helmet. The HMD places an image of both the physical world and virtual objects over the user's field of view. The HMD may employ sensors for six degrees of freedom monitoring that allow the system to align virtual information (the augmentation information) to the physical world and adjust accordingly with the user's head movements. Alternatively, the display of the augmented reality device can be rendered on a device resembling eyeglasses. Versions include eyewear that employ cameras to intercept the real world view and re-display its augmented view through the eye piece and devices in which the AR imagery is projected through or reflected off the surfaces of the eyewear lens pieces. Alternatively, the augmented reality device may be embodied by a head-up display which can show data, information, and images while the user views the real world.

The augmented reality device is for example configured to display visual information on its display, for example to display the visual information as an overlay to a real image acquired with the augmented reality device. A real image is understood to be an image describing the physical scene in the field of view of the augmented reality device. The display of the augmented reality device may be an entirely digital display (for example, a monitor or a screen upon which a digital image is projected), or an optical display, for example a transparent (e.g. glass or plastic) screen which is transparent for a user to view the real image and may in one example additionally serve as a projection screen for projecting digitally generated information onto, for example as augmentation information for augmenting the information content of the real image.

Alternatively or additionally, the augmenting information may be projected directly into an eye of the user. The augmentation information may thus be displayed as an overlay on the real image. Alternatively, the real image may be acquired digitally and rendered on a digital display of the augmented reality device, and the augmentation information may be displayed together (for example, simultaneously) with the digitally rendered real image.

The augmented reality device comprises a distance measurement unit for measuring a distance (also called depth) between the augmented reality device and a specific object which is for example located in the field of view of the augmented reality device. The distance is defined for example as a vector in two or three dimensions. The distance measurement unit for example functions on the principle of measuring distance by detecting light reflections of measurement light from a surface of a real object to at least one light sensor included in the augmented reality device. For example, the distance measurement unit has at least one detecting unit (such as a CCD sensor) for detecting reflections of the measurement light from the physical object. Additionally, the distance measurement unit may have at least one light source for emitting measurement light onto the physical object. Alternatively or additionally, the measurement light may be emitted by an external light source which is not part auf the augmented reality device. The measurement light may be in the visible or infrared wavelength range. The distance is measured based on the principle of triangulation (using for example two stereoscopic detecting units) or time-of-flight (using for example at least one—for example only one—detecting unit).

In a further (for example second) exemplary step, object position information is acquired which describes a position of an object in the tracking coordinate system. For example, the object position information indicates the position of the object in the tracking coordinate system or indicates that the object cannot be tracked. The object is at least one of a virtual object, for example the field of view (also called tracking volume) of the position tracking system, or a physical object, i.e. a real object. The physical object may be at least one of an anatomical body part of a patient (e.g. a limb or the patient's head) or a medical device (e.g. a marker device, a medical instrument or a patient bed).

If the object is a physical object which is tracked (i.e. positionally detected) by the position tracking system, the object position information may then describe for example a result of tracking the position of the physical object by the position tracking system in the tracking coordinate system. Object presence information may then be determined using a distance measurement by the distance measurement unit of the augmented reality device. The object presence information may then define a presence (or absence) of the physical object in (or from) the real image on the display of the augmented reality device. For example, the position tracking system is able to access information describing a property of the physical object (such as its type, user guidance for using the object, a warning associated with the object). Specifically, the position tracking system may be configured to identify the physical object, for example be identifying a unique geometry of a marker configuration of a marker device associated with (e.g. attached to) the physical object to thereby identify the object. The augmented reality device registration may be used to determine a relative position between the viewing direction of the augmented reality device and the position of the physical object. If this results in that the relative position fulfils a predetermined (e.g. at least one of known or fixed) condition, it is determined that the object lies in the field of view of the positional tracking system (and also in the line of sight of the augmented reality device, because it was able to detect the object with the distance measurement unit) and for example therefore in the real image.

In a (for example third) exemplary step, augmentation information is determined based on the object presence information and output by an output unit (e.g. a display unit or a projector unit) of the augmented reality device, for example displayed on a display (e.g. a display unit) of the augmented reality device or projected (for example, as optical information) by the augmented reality device (e.g. by a projector unit included in the augmented reality device) into an eye of a user (e.g. a user of the augmented reality device). The augmentation information is for example visual information which is graphically output on the display of the augmented reality device. For example, a transformation (i.e. a positional mapping, for example a linear function defining a mapping between positions and/or coordinate systems) is determined between the position of the physical object in the tracking coordinate system is transformed from the tracking coordinate system to the coordinate system used for displaying the augmentation information on the display of the augmented reality device. The augmentation information is then displayed on the display of the augmented reality device based on that transformation so that the augmentation information is displayed in a predetermined spatial relationship (i.e. at least one of position and orientation) in the display of the augmented reality device. If the object is a virtual object, the augmentation information may for example be displayed at a position in the real image corresponding to the position of the virtual object in the tracking coordinate system. If the object is a physical object, the augmentation information may be associated with the physical object and for example be displayed in a predetermined spatial relationship relative to the position of the physical object in the real image.

In examples, the augmentation information describes at least one of the following:
- the field of view of the position tracking system (for example, by defining a visual delineation (rendering) of the field of view in the real image);
- if the object is at least a physical object, the result of tracking the position of the physical object, for example whether a line of sight between the position tracking system and the physical object is obstructed;
- at least one visual indication (e.g. a text label or colouring, i.e. coloured encoding) describing an accuracy of the positional tracking by the position tracking system;
- if the object is at least a physical object, at least one visual indication (e.g. text label or colouring, i.e. coloured encoding) describing whether the physical object is meant to be tracked by the position tracking system, for example whether tracking the physical object is essential for correct functioning of an associated medical system;

if the object is at least a physical object, at least one visual indication (e.g. text label or colouring, i.e. coloured encoding) for identifying the physical object;

at least one visual indication (e.g. text label or colouring, i.e. coloured encoding) describing a warning to a user of the augmented reality device, for example if the object is at least a physical object, for example a warning not to touch the physical object or that the physical object is close to being out of a line of sight between the position tracking system and the physical object.

If the augmentation information describes the field of view of the position tracking system, for example field-of-view-position information is acquired by the disclosed method which defines the position (extent) of the field of view of the tracking system for example in the tracking coordinate system. The position of the field of view of the tracking system for example in the tracking coordinate system is then transformed into a coordinate system used by the augmented reality device for displaying information on its display. The transformation is based on and/or represented by the augmented reality device registration. The field-of-view-position information is for example predetermined (i.e. at least one of known or fixed) and can be acquired from the tracking coordinate system, for example from construction and/or control data of the tracking coordinate system.

For example, the augmentation information has been customized for a user of the augmented reality device, for example a subset of available augmentation information is displayed by the augmentation device and where the definition of the subset is determined by a user profile. The customization may encompass determining a role of the user in a medical environment such as an operating room, for example whether the user is an operating surgeon or an assistant such as a nurse or junior surgeon. Accordingly, information may be selected as augmentation information for the user as required by his role. For example, an assistant as a user may be displayed a warning to stand clear of a certain physical object such as a specific instrument, while the operating surgeon may be displayed guidance information how to use a specific instrument embodying the physical structure.

The augmented reality device registration may be generated according to at least one of the following examples 1 to 7 for positionally registering the augmented reality device with the tracking coordinate system:

Example 1 for Positionally Registering the Augmented Reality Device with the Tracking Coordinate System In this example, the object is at least a physical object and the position tracking system in this example is an infra-red tracking system and an infrared-reflective marker device is attached to the physical object in a predetermined (at least one of known or fixed) position relative to the physical object for allowing tracking of the physical object by the position tracking system. Alternatively, the position tracking system is an electromagnetic tracking system and an electromagnetic marker device (an array of resonator coils) is attached to the physical object in a predetermined (at least one of known or fixed) position relative to the physical object for allowing tracking of the physical object by the position tracking system. The (infrared-reflective or electromagnetic) marker device is then tracked by the position tracking system, for example by emitting infrared light onto the infrared-reflective marker device or by emitting electromagnetic waves in the resonance range of the array of resonator coils onto the electromagnetic marker device, and detecting the signal returned from the respective marker device in space, for example using a multi-dimensional positional detector such as an infrared-sensitive stereoscopic camera or an array of electromagnetic detection circuits.

In this example, the method may comprise for example the following steps:

marker device template data is acquired (for example, from constructional data of the marker device such as computer-aided design data) which describes a geometrical template of the marker device (e.g. a geometrical configuration of the marker device defined by the constructional data);

surface detection data which describes a surface geometry of the marker device is acquired based on a distance measurement by the distance measurement unit of the augmented reality device (for example, the distance measurement unit is used to scan the surface of the marker device, and a surface model of the marker device is generated based on the scanned surface points on the surface of the marker device according to their respectively determined distance from the augmented reality device);

a relative position between the augmented reality device and the marker device is determined based on the surface detection data and the marker device template data (for example, by comparing the surface appearance of the marker device according to the surface detection data and the marker device template data, respectively, taking into account the determined distance between the marker device and the augmented reality device and/or the distance measurement unit);

the viewing direction of the augmented reality device is positionally registered with the position tracking coordinate system based on the determined relative position between the augmented reality device and the marker device.

For example, the augmented reality device registration is then determined based on the distance between the augmented reality device and the marker device and the position of the marker device tracked (determined) by the position tracking system according to known operations of linear algebra.

Example 2 for Positionally Registering the Augmented Reality Device with the Tracking Coordinate System In this example, the object is at least a physical object and the method comprises the following steps:

physical object template data is acquired which describes a geometrical template of the physical object;

surface detection data which describes a surface geometry of the physical object is acquired based on a distance measurement by the distance measurement unit (for example, the distance measurement unit of the augmented reality device is used to scan the surface of the physical object, and a surface model of the physical object is generated based on the scanned surface points on the surface of the physical object according to their respectively determined distance from the augmented reality device);

a relative position between the augmented reality device and the physical object is determined based on the surface detection data and the physical object template data (for example, by comparing the surface appearance of the physical object according to the surface detection data and the marker device template data, respectively, taking into account the determined distance between the physical object and the augmented reality device and/or the distance measurement unit);

the viewing direction of the augmented reality device is positionally registered with the tracking coordinate system based on the determined relative position between the augmented reality device and the physical object.

For example, the position of the physical object is tracked by the position tracking system, for example by tracking the position of a marker device attached to the physical object in a predetermined (i.e. at least one of known or fixed) spatial relationship (i.e. at least one of position and orientation) relative to the physical object. For example, the augmented reality device registration is then determined based on the distance between the augmented reality device and the physical object and the position of the physical object tracked (determined) by the position tracking system according to known operations of linear algebra.

If the physical object is anatomical body part, the physical object template data may be acquired from a patient image taken for the specific patient. The patient image is for example a three-dimensional data set taken with a tomographic imaging modality such as computed x-ray tomography or magnetic resonance tomography or ultrasound tomography. Alternatively or additionally, the physical template data may be acquired from atlas data describing a generic geometrical model of the anatomical body part, or from an individual synthetic template describing a synthesized geometric model of the anatomical body part (which has been generated for example only for the specific patient).

If the physical object is a device such as a medical device (e.g. an instrument or a patient bed or at least a part of the tracking system such as the multi-dimensional position detector, e.g. the stereoscopic camera or array of electromagnetic detection circuits) the physical object template data may be acquired from constructional data such as computer-aided design data of the device.

Example 3 for Positionally Registering the Augmented Reality Device with the Tracking Coordinate System In this example, the object is at least a physical object, and the position tracking system has a distance measurement unit (for example working on one of the measurement principles used or usable by the distance measurement unit of the augmented reality device). In this example, the method comprises the following steps:

surface detection tracking data which describes a surface geometry of the physical object is acquired based on a distance measurement by the distance measurement unit of the tracking system (for example, the distance measurement unit of the tracking system is used to scan the surface of the physical object, and a surface model of the physical object is generated based on the scanned surface points on the surface of the physical object according to their respectively determined distance from the position tracking system and/or the distance measurement unit of the position tracking system);

surface detection data which describes a surface geometry of the physical object is acquired based on a distance measurement by the distance measurement unit of the augmented reality device (for example, the distance measurement unit of the augmented reality device is used to scan the surface of the physical object, and a surface model of the physical object is generated based on the scanned surface points on the surface of the physical object according to their respectively determined distance from the augmented reality device);

the viewing direction of the augmented reality device is positionally registered with the tracking coordinate system
a. based on the surface detection data and the surface detection tracking data and
b. based on the distance measurements by the distance measurement unit of the position tracking system and the distance measurement unit of the augmented reality device.

For example, the surface models of the physical object generated based on the measurements of the distance measurement unit of the augmented reality device and the distance measurement unit of the position tracking system, respectively, are compared using a known algorithm such as the iterative closest point algorithm (ICP) or robust point matching algorithm (RPM), taking into account the distance between the distance measurement unit and the physical object. Thereby, the appearances of the physical object in each of the two surface models can be made comparable, and on the basis of the comparison by searching the scan image output of at least one of the distance measurement units for the model appearance of the physical object in the scan image output of the other one of the two distance measurement units, the position of the physical object can be determined. By knowing the distance between the augmented reality device and the physical object on the one hand and the distance between the position tracking system and/or the distance measurement unit of the position tracking system and the physical object on the other hand, the relative position between the augmented reality device and the position tracking system can be determined so that the position of the augmented reality device in the tracking coordinate system becomes known, thereby generating the augmented reality device registration.

Example 4 for Positionally Registering the Augmented Reality Device with the Tracking Coordinate System In this example, the augmented reality device is tracked by the position tracking system. For example, an infrared-reflective marker device or an electromagnetic marker device is attached to the augmented reality device, for example in a predetermined (i.e. at least one of known or fixed) spatial relationship (i.e. at least one of position or orientation) between the marker device and the viewing direction of the augmented reality device. The viewing direction of the augmented reality device is positionally registered with the tracking coordinate system based on the result of tracking the augmented reality device, for example based on information about the predetermined (i.e. at least one of known or fixed) spatial relationship (i.e. at least one of position or orientation) between the marker device and the viewing direction of the augmented reality device.

Example 5 for Positionally Registering the Augmented Reality Device with the Tracking Coordinate System In this example, the augmented reality device comprises a visible image acquisition unit (e.g. a video or still camera)

for acquiring an image (for example, a digital image) in the visible wavelength range, and wherein the method comprises the following steps:

- tracking system surface template data is acquired which describes a geometrical template of at least the surface of at least part of the position tracking system (for example, the multi-dimensional position detector such as the stereotactic camera or array of resonant coil circuits);
- an image describing at least part of the tracking system is obtained from the visible image acquisition unit;
- the viewing direction of the augmented reality device is positionally registered with the tracking coordinate system based on the tracking system template data and the image describing the at least part of the position tracking system.

The tracking system surface template data may be acquired from constructional data describing at least the surface geometry of the at least part of the position tracking system, for example computer-aided design data used for constructing the at least part of the position tracking system.

For example, the position of the at least part of the tracking system is determined in the image obtained from the visible image acquisition unit by comparing the surface appearance of the geometrical template of the at least part of the position tracking system with the content of the image obtained from the visible image acquisition unit. The distance between the augmented reality device and the at least part of the tracking system can be determined by analysing any potential size deviation in the appearance of the at least part of the tracking system in the image compared to its geometrical template.

By knowing the distance between the augmented reality device and the at least part of the tracking system on the one hand and the (predetermined, i.e. at least one of known or fixed) position of the at least part of the position tracking system in the tracking coordinate system on the other hand, the relative position between the augmented reality device and the position tracking system can be determined so that the position of the augmented reality device in the tracking coordinate system becomes known, thereby generating the augmented reality device registration.

Example 6 for Positionally Registering the Augmented Reality Device with the Tracking Coordinate System In this example, the method comprises the following steps:

- tracking system surface template data is acquired which describes a geometrical template of at least part of the position tracking system (for example, the multi-dimensional position detector such as the stereotactic camera or array of resonant coil circuits);
- tracking system surface detection data is acquired which describes a surface geometry of the at least part of the position tracking system based on a distance measurement by the distance measurement unit of the augmented reality device;
- the viewing direction of the augmented reality device is positionally registered with the tracking coordinate system based on the tracking system surface template data and the tracking system surface detection data.

The tracking system surface template data may be acquired from constructional data describing at least the surface geometry of the at least part of the position tracking system, for example computer-aided design data used for constructing the at least part of the position tracking system.

For example, the tracking system surface detection data is acquired based on the output obtained by using the distance measurement unit of the augmented reality device to scan the surface of the at least part of the position tracking system, and a surface model of the physical object. The tracking system surface detection data is generated based on the scanned surface points on the surface of the at least part of the position tracking system according to their respectively determined distance from the augmented reality device).

For example, the position of the at least part of the tracking system is determined in the scan output obtained from the distance measurement unit of the augmented reality device by comparing the surface appearance of the geometrical template of the at least part of the position tracking system with the scan output. The distance between the augmented reality device and the at least part of the position tracking system can be determined by analysing any potential size deviation in the appearance of the at least part of the tracking system in the scan output compared to its geometrical template.

By knowing the distance between the augmented reality device and the at least part of the tracking system on the one hand and the (predetermined, i.e. at least one of known or fixed) position of the at least part of the position tracking system in the tracking coordinate system on the other hand, the relative position between the augmented reality device and the position tracking system can be determined so that the position of the augmented reality device in the tracking coordinate system becomes known, thereby generating the augmented reality device registration.

Example 7 for Positionally Registering the Augmented Reality Device with the Tracking Coordinate System In this example, the augmented reality device comprises a visible image acquisition unit for acquiring an image in the visible wavelength range, and the method comprises the following steps:

- code pattern template data is acquired which describes a template of a code pattern attached to at least part of the position tracking system (for example, the multi-dimensional position detector such as the stereotactic camera or array of resonant coil circuits);
- a code pattern image describing the code pattern attached to the at least part of the position tracking system is obtained from the visible image acquisition unit;
- the viewing direction of the augmented reality device is positionally registered with the tracking coordinate system based on the code pattern template data and code pattern image.

The code pattern may be a visible code such as a bar code or QR (quick response) code, and the augmented reality device or an external computer communicatively coupled to the augmented reality device may be configured to analyze the code pattern image for the information encoded by the code pattern. The code pattern may comprise information for identifying (determining the identity of) the at least part of the tracking system.

The relative position between the augmented reality device and the positional tracking system is determined by computing the position and orientation of the code pattern relative to the augmented reality device. This is done by iteratively applying linear algebra methods, e.g. the POSIT algorithm (DeMenthon & Davis 1994).

In a further example of the method according to the first aspect, the position tracking system is a structured light tracking system, or comprises an articulable arm positionally registered with the tracking coordinate system.

In a further example of the method according to the first aspect, the object presence information is determined based on generating a three-dimensional scene using distance measurements by the distance measurement unit of the augmented reality device and the augmented reality device registration.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer is operably coupled to the program storage medium according to the third aspect for executing the program stored on the program storage medium.

In a fifth aspect, the invention is directed to a (physical, for example electrical, for example technically generated) signal wave, for example a digital signal wave, carrying information which represents the program according to the second aspect.

In a sixth aspect, the invention is directed to a medical system for determining augmentation information relating to positional tracking by a medical position tracking system, the medical system comprising:
- the at least one computer according to the fourth aspect; and
- the position tracking system for tracking the position of a physical object; and
- an augmented reality device having a distance measurement unit and an output unit for outputting the augmentation information.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of therapy or surgery. More particularly, the invention does not involve or in particular comprise or encompass any surgical or therapeutic activity. The invention is instead directed as applicable to reading and processing data and operating or controlling a computer to execute a program which causes the computer to perform the data processing method according to the first aspect. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

In an example, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained once or twice or more over time.

A navigation system (within this disclosure also called position tracking system), such as a surgical navigation system, is understood to mean a system which can comprise: at least one marker device (such as the above-mentioned infrared-reflecting marker device or electromagnetic marker device); a transmitter which emits electromagnetic waves and/or radiation and/or ultrasound waves onto the at least one marker device; a receiver (such as the above-identified multi-dimensional position detector, for example the infrared-sensitive stereotactic camera or array of resonant coil circuits) which receives electromagnetic waves and/or radiation and/or ultrasound waves from the at least one marker device; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand. The position of the at least one marker device can be determined by the data processing device from the electromagnetic waves and/or radiation and/or ultrasound waves received by the receiver.

DESCRIPTION OF THE FIGURES

In the following, the invention is described with reference to the appended figures which represent a specific embodiment of the invention. The scope of the invention is however not limited to the specific features disclosed in the context of the figures, wherein

Figure 1:
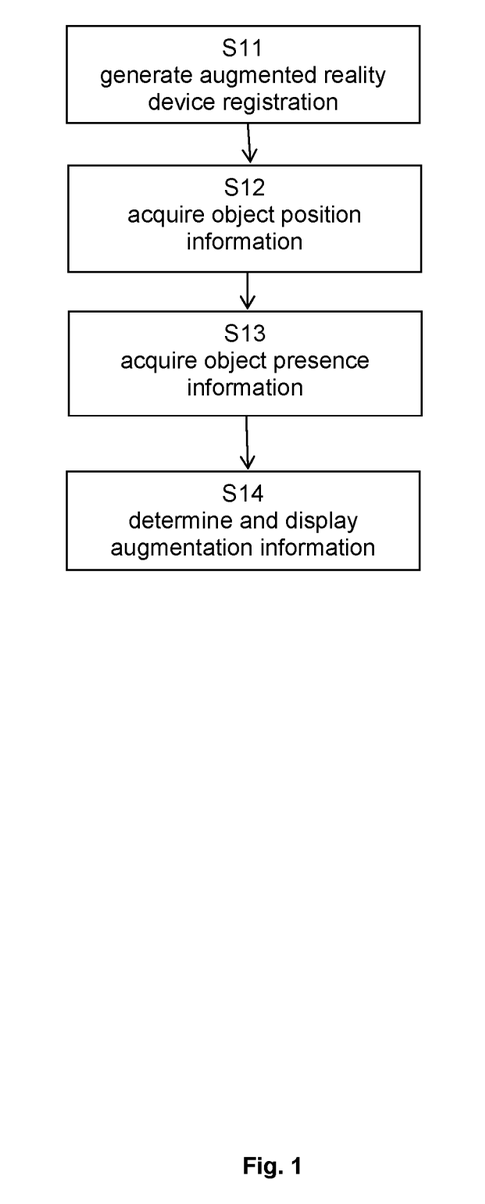
FIG. 1 is a flow diagram illustrating the basic steps of the method according to the first aspect.

FIG. 1 shows the basic flow of the method according to the first aspect, which starts with a step S11 of generating the augmented reality device registration, followed by a step S12 of acquiring the object position information. In subsequent step S13, the object presence information is acquired, followed by a final step S14 of determining and displaying the augmentation information.

Figure 2:
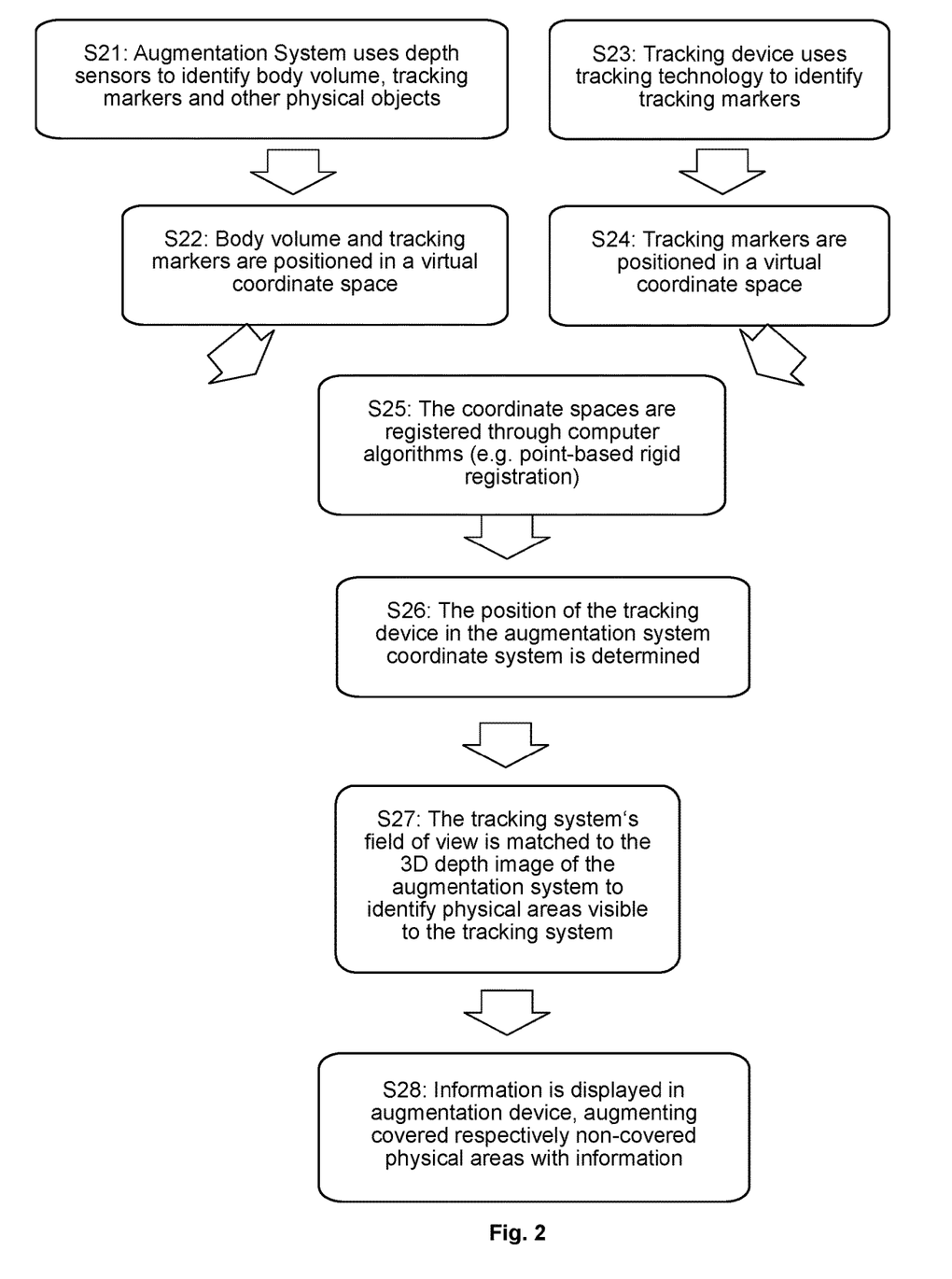
FIGS. 2 to 5 illustrate four examples of generating the augmented reality device registration.

FIG. 2 shows a first way of specifying the steps of FIG. 1. In step S21, the augmentation system (augmented reality device 4) uses its distance measurement unit (depth sensor) to identify a body volume corresponding to an anatomical body part or a tracking markers (marker device) or other physical object 6 by measuring a distance between the distance measurement unit and the body volume or the tracking markers or other physical object 6, respectively. The result is obtained in step S22 as the position of the body volume or the tracking markers (a marker device) or other physical object 6, respectively, in a virtual coordinate space (coordinate system) associated with the augmented reality device 5. Steps S23 and S24 may be executed subsequently, before or in parallel to (simultaneously with) steps S21 and S22. Step S21 encompasses position tracking (identification) of the tracking markers by a tracking device embodying the position detector 4 of the position tracking system 2. The result of the tracking is obtained in step S24 as a position of the tracking markers in a virtual coordinate space associated with the position tracking system 2, namely the tracking coordinate system. In step S25, the two virtual coordinate spaces are registered with one another (i.e. the spatial relationship, in particular transformation of bases between the two coordinate spaces is determined, for example by point-based rigid registration).

In subsequent step S26, the position of the tracking device is determined in the coordinate system associated with the augmented reality device 5. In step S27, the field of view of the tracking system 2 is matched to the three-dimensional depth image (generated by the distance measurement using the distance measurement unit of the augmented reality device 5) to identify a physical area visible to the tracking system (i.e. to identify the field of view of the position tracking system 2 in the real image acquired by the augmented reality device 5). In step S28, this match is used to display information (the augmentation information) in the augmented reality device (also called augmentation device or augmentation system) 5, for example to augment areas in the real image covered or non-covered, respectively, by the field of view of the tracking system 2, with augmentation information.

Figure 3:
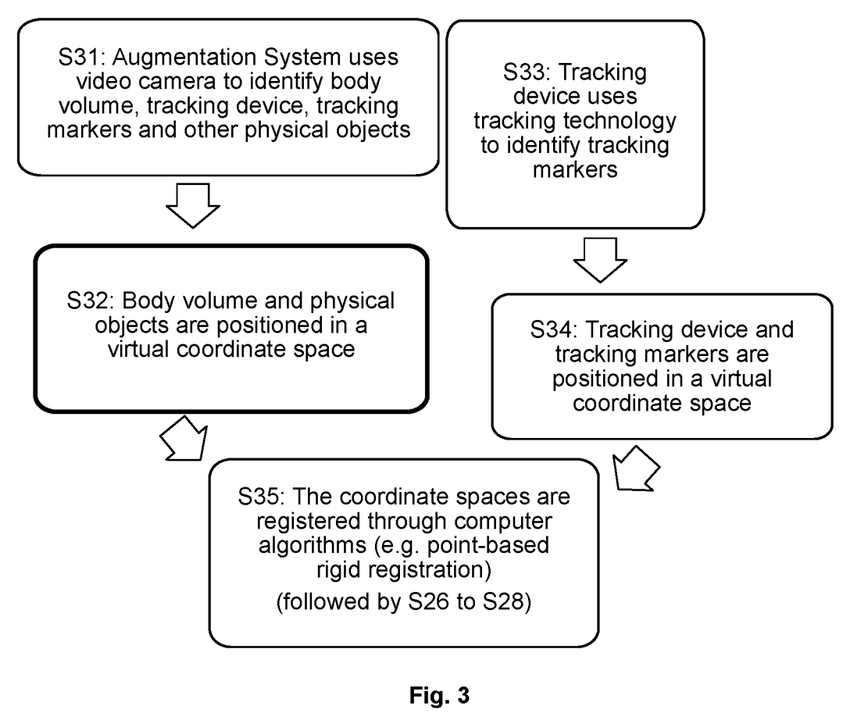

FIG. 3 shows a variation of the example of FIG. 2 in which step S31 encompasses the augmented reality device 5 using a video camera to identify a body volume, a tracking device, a marker device (tracking marker) or another physical object 6. Subsequently, the position of the body volume and the physical object is determined in a virtual coordinate space associated with the augmented reality device 5. Steps S33 and S34 may be executed before, after or in parallel to (i.e. simultaneously with) steps S31 and S32. Steps S33 and S34 correspond to steps S23 and S24, respectively, of FIG. 2. Subsequent step S35 corresponds to step S25 of FIG. 2, and is followed by steps S26 to S28 of FIG. 2.

Figure 4:
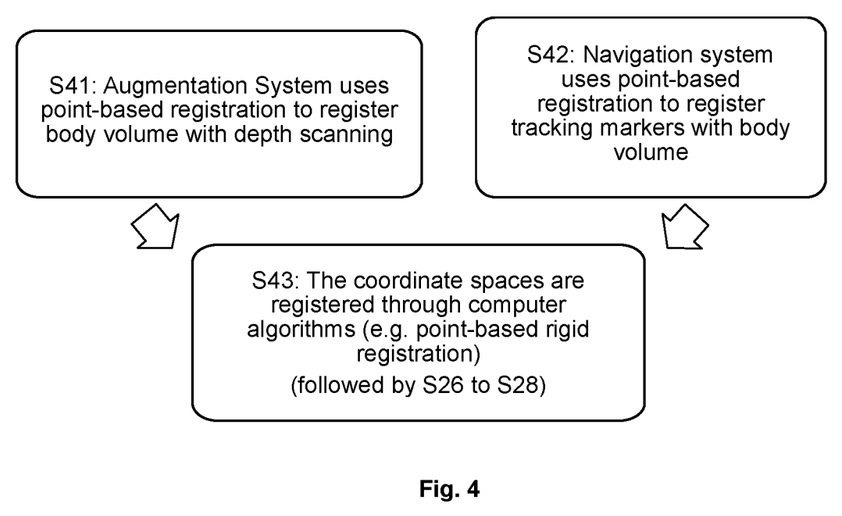

FIG. 4 shows a further variation of the example of FIG. 2 in which step S41 encompasses the augmented reality device 5 using point-based registration to register a body volume by depth scanning (i.e. surface scanning using the distance measurement unit of the augmented reality device 5). Step S42 may be executed before, after or in parallel to (i.e. simultaneously with) step S41. Subsequent step S43 corresponds to step S25 of FIG. 2, and is followed by steps S26 to S28 of FIG. 2.

Figure 5:
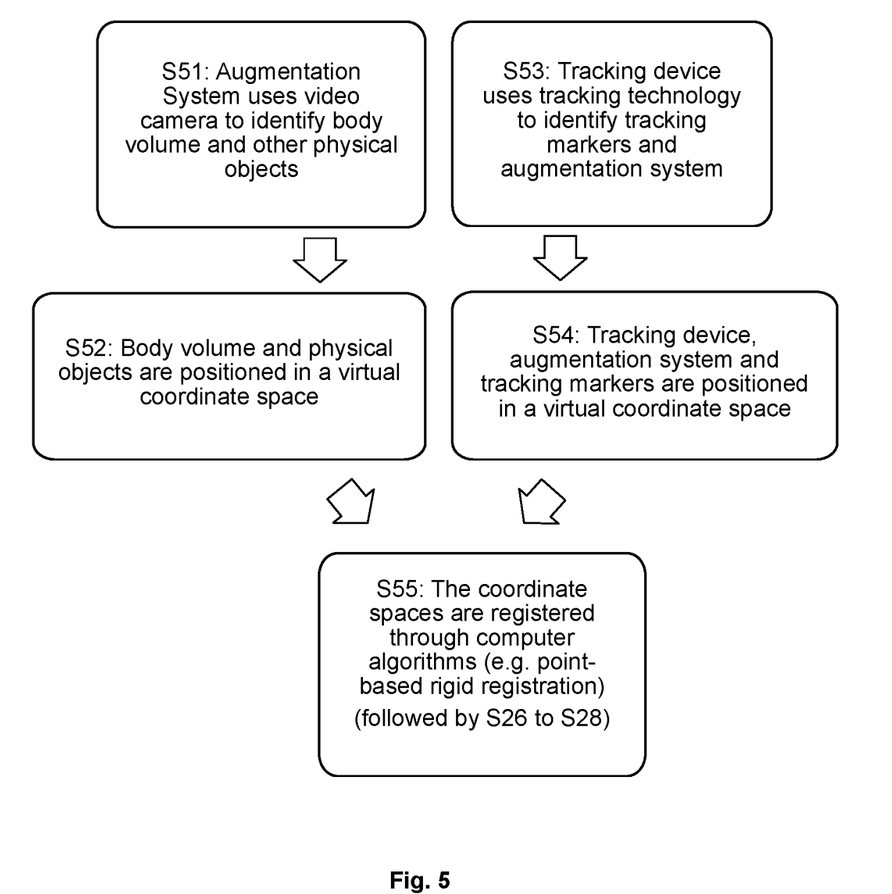

FIG. 5 shows a combination of an even further variation of the example of FIG. 2 with a variation of the example of FIG. 3 in which steps S51 and S52 correspond to steps S31 and S32, respectively. S51 encompasses the augmented reality device 5 using point-based registration to register a body volume by depth scanning (i.e. surface scanning using the distance measurement unit of the augmented reality device). Steps S53 and S54 may be executed before, after or in parallel to (i.e. simultaneously with) steps S51 and S52. In step S53, the position tracking system 2 identifies both the marker device and the augmentation system (by applying the respective tracking technology). The result of step S53 is determined in step S54 by determining the position of the marker device and the position of the augmented reality device 5 in step S54 in a virtual coordinate space associated with the position tracking system 2 (the tracking coordinate system). Subsequent step S55 corresponds to step S25 of FIG. 2, and is followed by steps S26 to S28 of FIG. 2.

Figure 6:
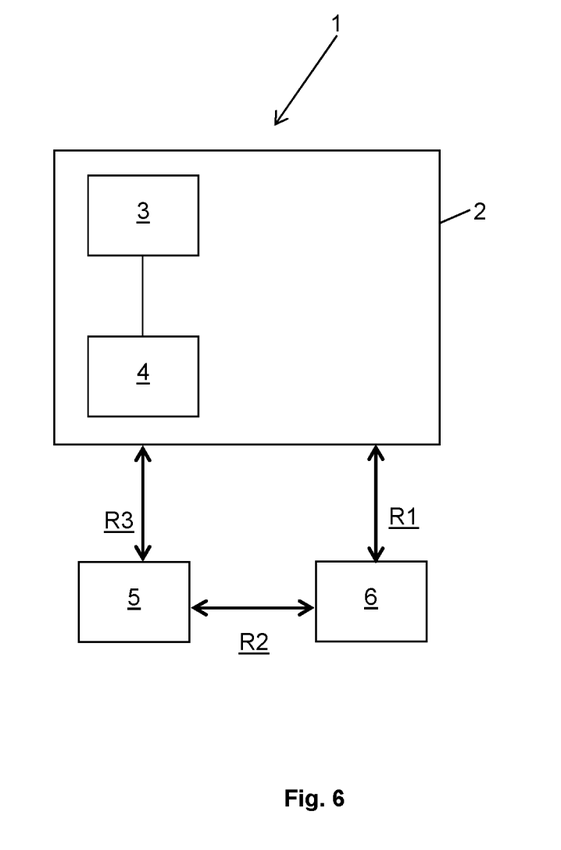
FIG. 6 illustrates the setup of the medical system according to the sixth aspect.

FIG. 6 gives a schematic overview of the medical system 1 according to the sixth aspect. The medical system 1 comprises a position tracking system 2 which comprises a computer 3 which is operably coupled to a multi-dimensional position detector 4. The augmented reality device 5 and optionally a physical object 6 are also part of the medical system 1. Within the framework of this disclosure, examples are given for determining a registration (relative position) R1 between the position tracking system 2 and the physical object 6, a registration (relative position) R2 between the physical object 6 and the augmented reality device 5, and a registration (relative position) R3 between the augmented reality device 5 and the position tracking system 2.

Figure 7:
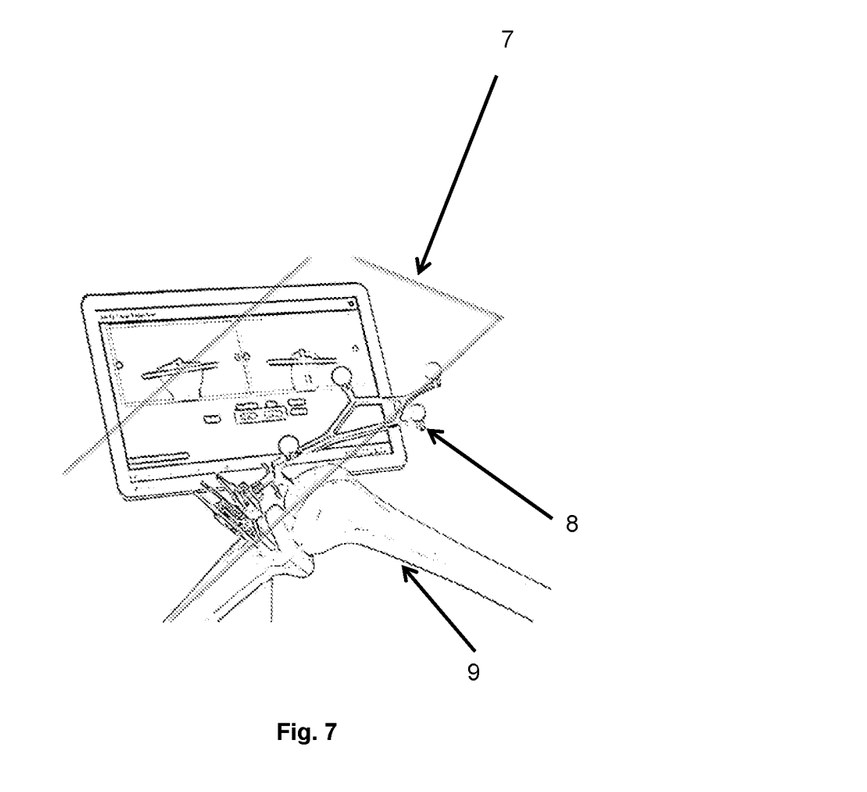
FIG. 7 illustrates an example of the augmentation information.

FIG. 7 shows an example of augmentation information embodied by a graphical representation of the field of view 7 of the position tracking system 2 which is overlaid onto a real image depicting a marker device 8 and an anatomical body part 9 comprising a part of a lower limb. As can be seen from FIG. 7, the marker device 8 is at least partly within the field of view of the field of view 7.

The method according to the first aspect may be summarized as follows:

First a correspondence of the coordinate systems of the tracking device and the augmentation system needs to be determined.

One of the following methods (or a combination thereof) may be applied:

The augmentation system identifies a tracking marker (assembly) through the use of video cameras The augmentation system identifies a body volume via depth sensors that is registered to tracking markers The augmentation system identifies a volume via depth sensors that is also picked by depth sensors contained in the tracking system The augmentation system possesses tracking markers itself The augmentation system identifies the tracking device itself through video cameras or depth sensors.

Based on the established correspondence, otherwise invisible aspects related to the tracking device can be augmented to the user's view by converting virtual objects from the tracking device into the augmentation coordinate system.

This can further comprise mapping this information on to a surface picked up by the depth sensors or determining the shadow area of objects depicted by the depth sensors of the augmentation system which might be invisible to the tracking device.

The tracking device may be an infra-red tracking device (usable in surgery or radiotherapy), an E/M (electromagnetic) tracking device, articulated arm or any other tracking device. The augmentation device could be any device with the ability to use another tracking method from a different direction. The second device incorporates a display, e.g. a head-mounted display in glasses worn by the user.

To improve surgical navigation or patient positioning in radiotherapy the following could be calculated and displayed on the augmented reality device, specifically in augmented reality glasses:

The volume currently captured by the tracking system (i.e. its field of view) is displayed. Vice-versa areas currently not seen by the surgical navigation system can be marked.

Labels noting the estimated tracking accuracy can be displayed, e.g. on the edges of an EM tracking area Markers or devices currently not seen by the tracking system but essential for correct utilization are labeled so that the user understands that they are not seen.

Objects that currently obstruct the tracking systems' line of sight (e.g. surgeons' hands) can be marked and the shadow that they are casting with respect to the tracking device can be displayed.

Devices seen by the surgical navigation system can be annotated with their labels.

Warnings can be displayed during the procedure, e.g. warnings to avoid contact with reference arrays.

If multiple augmented devices are in use, the specific content displayed in each device can be individually determined, e.g. by displaying accuracy warnings in the assistant's display and no warnings in the surgeon's display.

The invention claimed is:

1. A computer-implemented medical method for outputting, by an augmented reality device having a distance measurement unit and a display, augmentation information relating to positional tracking by a medical position tracking system, the method comprising executing, on at least one processor of at least one computer, the following steps:

a) a viewing direction of the augmented reality device is positionally registered with a tracking coordinate system associated with the position tracking system to generate an augmented reality device registration;

b) object position information is acquired which describes a position of a physical object in the tracking coordinate system, tracked by the position tracking system;

c) object presence information defining a presence of the physical object in a field of view of the augmented reality device is determined, using the distance measurement unit of the augmented reality device that determines a position of the augmented reality device relative to the physical object, and based on the augmented reality device registration and the object position information;

d) augmentation information is determined based on the object presence information and output by the display of the augmented reality device, wherein the augmentation information describes a tracking volume of the position tracking system by defining a visual rendering of the field of view of the position tracking system on the display of the augmented reality device, wherein a position of the field of view is transformed from the tracking coordinate system to a virtual coordinate space associated with the augmented reality device; and wherein the position of the physical object in the tracking coordinate system is transformed from the tracking coordinate system to the virtual coordinate space associated with the augmented reality device, the virtual coordinate space usable for displaying the augmentation information on the display of the augmented reality device, wherein the augmentation information at least describing the tracking volume of the position tracking system is displayed as an overlay with respect to the physical object on the display of the augmented reality device and provides the visual rendering that indicates the position of the field of view.

2. The method according to claim 1, wherein the augmentation information further describes at least one of the following:
a result of tracking the position of the physical object, whether a line of sight between the position tracking system and the physical object is obstructed;
at least one visual indication describing whether the physical object is meant to be tracked by the position tracking system, whether tracking the physical object is essential for correct functioning of an associated medical system;
at least one visual indication for identifying the physical object; and
at least one visual indication describing a warning to a user of the augmented reality device, a warning not to touch the physical object or that the physical object is close to being out of a line of sight between the position tracking system and the physical object.

3. The method according to claim 1 wherein
the position tracking system is an infra-red tracking system and an infrared-reflective marker device is attached to the physical object in a predetermined position relative to the physical object for allowing tracking of the physical object by the position tracking system, or
wherein the position tracking system is an electromagnetic tracking system and an electromagnetic marker device is attached to the physical object in a predetermined position relative to the physical object for allowing tracking of the physical object by the position tracking system.

4. The method according to claim 3 comprising the following steps:
marker device template data is acquired which describes a geometrical template of the marker device;
surface detection data which describes a surface geometry of the marker device is acquired based on a distance measurement by the distance measurement unit;
a relative position between the augmented reality device and the marker device is determined based on the surface detection data and the marker device template data; and
the viewing direction of the augmented reality device is positionally registered with the tracking coordinate system based on the determined relative position between the augmented reality device and the marker device.

5. The method according to claim 3, comprising the following steps:
physical object template data is acquired which describes a geometrical template of the physical object;
surface detection data which describes a surface geometry of the physical object is acquired based on a distance measurement by the distance measurement unit;
a relative position between the augmented reality device and the physical object is determined based on the surface detection data and the physical object template data; and
the viewing direction of the augmented reality device is positionally registered with the tracking coordinate system based on the determined relative position between the augmented reality device and the physical object.

6. The method according to claim 1 wherein the augmented reality device comprises a visible image acquisition unit for acquiring an image in a visible wavelength range, and wherein the method comprises the following steps:
tracking system surface template data is acquired which describes a geometrical template of at least the surface of at least part of the position tracking system;
an image describing at least part of the tracking system is obtained from the visible image acquisition unit; and
the viewing direction of the augmented reality device is positionally registered with the tracking coordinate system based on the tracking system template data and the image describing the at least part of the position tracking system.

7. The method according to claim 1 wherein the method comprises the following steps:
tracking system surface template data is acquired which describes a geometrical template of at least part of the position tracking system;
tracking system surface detection data is acquired which describes a surface geometry of the at least part of the position tracking system based on a distance measurement by the distance measurement unit of the augmented reality device; and
the viewing direction of the augmented reality device is positionally registered with the tracking coordinate system based on the tracking system surface template data and the tracking system surface detection data.

8. A non-transitory computer-readable medium storing statements and instructions for execution by a computer to perform a method comprising steps of:
a) a viewing direction of an augmented reality device is positionally registered with a tracking coordinate system associated with a position tracking system to generate an augmented reality device registration;
b) object position information is acquired which describes a position of a physical object in the tracking coordinate system, tracked by the position tracking system;
c) object presence information defining a presence of the physical object in a field of view of the augmented reality device is determined, using a distance measurement unit of the augmented reality device that determines a position of the augmented reality device to the physical object, and based on the augmented reality device registration and the object position information;
d) augmentation information is determined based on the object presence information and output by a display of the augmented reality device, wherein the augmentation information describes a tracking volume of the position tracking system by defining a visual rendering of the field of view of the position tracking system on the display of the augmented reality device, wherein a position of the field of view is transformed from the tracking coordinate system to a virtual coordinate space associated with the augmented reality device; and
wherein the position of the physical object in the tracking coordinate system is transformed from the tracking coordinate system to the virtual coordinate space associated with the augmented reality device, the virtual coordinate space usable for displaying the augmentation information on the display of the augmented reality device, wherein the augmentation information at least describing the tracking volume of the position tracking system is displayed as an overlay with respect to the physical object on the display of the augmented reality device and provides the visual rendering that indicates the position of the field of view.

9. A medical system for determining augmentation information relating to positional tracking by a medical position tracking system, the medical system comprising:
at least one computer;
the medical position tracking system for tracking a position of a physical object; and
an augmented reality device having a distance measurement unit and an output unit for outputting augmentation information,
wherein the at least one computer includes at least one processor and memory storing instructions that, when executed, cause the at least one processor to perform following steps:
a) a viewing direction of the augmented reality device is positionally registered with a tracking coordinate system associated with the position tracking system to generate an augmented reality device registration;
b) object position information is acquired which describes a position of a physical object in the tracking coordinate system, tracked by the position tracking system;
c) object presence information defining a presence of the physical object in a field of view of the augmented reality device is determined, using the distance measurement unit of the augmented reality device that determines a position of the augmented reality device relative to the physical object, and based on the augmented reality device registration and the object position information;
d) augmentation information is determined based on the object presence information and output by a display of the augmented reality device, wherein the augmentation information describes a tracking volume of the position tracking system by defining a visual rendering of the field of view of the position tracking system on the display of the augmented reality device, wherein a position of the field of view is transformed from the tracking coordinate system to a virtual coordinate space associated with the augmented reality device, on the display of the augmented reality device; and
wherein the position of the physical object in the tracking coordinate system is transformed from the tracking coordinate system to the virtual coordinate space associated with the augmented reality device, the virtual coordinate space usable for displaying the augmentation information on the display of the augmented reality device, wherein the augmentation information at least describing the tracking volume of the position tracking system is displayed as an overlay with respect to the physical object on the display of the augmented reality device and provides the visual rendering that indicates the position of the field of view.

10. A computer implemented method, comprising:
positionally registering a field of view of an augmented reality device with a position tracking system that tracks objects in a tracking coordinate system, the tracking coordinate system being associated with the position tracking system;
acquiring object position information of a physical object in the tracking coordinate system and tracked by the position tracking system,
determining object presence information representing the position of the physical object in the field of view of the augmented reality device using a position determination unit associated with the augmented reality device; and
determining augmentation information using at least the object presence information, the augmentation information describing a tracking volume of the position tracking system to be displayed via the augmented reality device by defining a visual rendering of at least a part of the field of view of the position tracking system on a display of the augmented reality device, wherein a position of the tracking volume is transformed from the tracking coordinate system associated with the position tracking system to a virtual coordinate space of the augmented reality device,
the augmentation information describing at least a part of the tracking volume of the position tracking system as an overlay with respect to the physical object and
providing a visual rendering indicating the position of the field of view.

* * * * *